United States Patent
Yates

[19]

[11] Patent Number: 6,106,287
[45] Date of Patent: Aug. 22, 2000

[54] FILTER SYSTEM FOR COUPLING OF A DENTAL HANDPIECE

[76] Inventor: Davis Yates, 1826 Stonecrest Ct., Lakeland, Fla. 33813

[21] Appl. No.: 09/267,855

[22] Filed: Mar. 12, 1999

Related U.S. Application Data

[63] Continuation-in-part of application No. 09/209,579, Dec. 11, 1998, abandoned.

[51] Int. Cl.[7] .................................................. A61C 17/02
[52] U.S. Cl. .............................. 433/82; 433/80; 604/190
[58] Field of Search ................................ 433/80, 82, 91; 604/190

[56] References Cited

U.S. PATENT DOCUMENTS

| | | |
|---|---|---|
| 2,605,019 | 7/1952 | Cornelius . |
| 2,950,030 | 8/1960 | McConnohie . |
| 3,894,338 | 7/1975 | Loge et al. . |
| 3,977,560 | 8/1976 | Stumfe et al. . |
| 4,035,303 | 7/1977 | Ufferfilge . |
| 4,217,101 | 8/1980 | Loge ......................................... 433/82 |
| 4,225,060 | 9/1980 | Kutik et al. . |
| 4,260,382 | 4/1981 | Thomson ................................ 433/126 |
| 4,950,159 | 8/1990 | Hansen ...................................... 433/80 |
| 5,033,961 | 7/1991 | Kandler et al. . |
| 5,204,004 | 4/1993 | Johnston .................................... 433/80 |
| 5,474,451 | 12/1995 | Dalrymple et al. ....................... 433/80 |
| 5,556,279 | 9/1996 | Wolf et al. ................................ 433/82 |
| 5,709,545 | 1/1998 | Johnston ................................... 433/80 |
| 5,716,210 | 2/1998 | Novak ....................................... 433/80 |
| 5,733,117 | 3/1998 | Coss et al. ................................ 433/82 |
| 5,749,726 | 5/1998 | Kinsel ....................................... 433/80 |

FOREIGN PATENT DOCUMENTS

| | | | |
|---|---|---|---|
| 31 126 | 7/1981 | European Pat. Off. ................. 433/82 |
| 2 118 837 | 11/1983 | United Kingdom ..................... 433/82 |

*Primary Examiner*—Ralph A. Lewis
*Attorney, Agent, or Firm*—Larson & Larson, P.A.; James E. Larson

[57] ABSTRACT

A filter system for coupling of dental handpiece is contemplated for use within a coupling system supplying air and water to a dental handpiece. The coupling system includes a swivel coupling including a series of axially and radially spaced annular couplings on an adapter, each of which supplies one of water, air supply, tool drive air supply or conveys exhaust air. The adapter permits use with standard handpieces. The filter consists of a small filter plate mounted under a cap at the proximal end of the coupling at the distal end of a chamber that receives water from the water source. Water from the water source is conveyed into the chamber, passes through the filter plate, and is conveyed through the coupling to the handpiece where it may be sprayed in the patient's mouth. A cap is threadably mounted on the coupling to close the chamber and the cap may be removed to either clean or replace the filter. The entire assembly may be autoclaved as a unit.

23 Claims, 8 Drawing Sheets

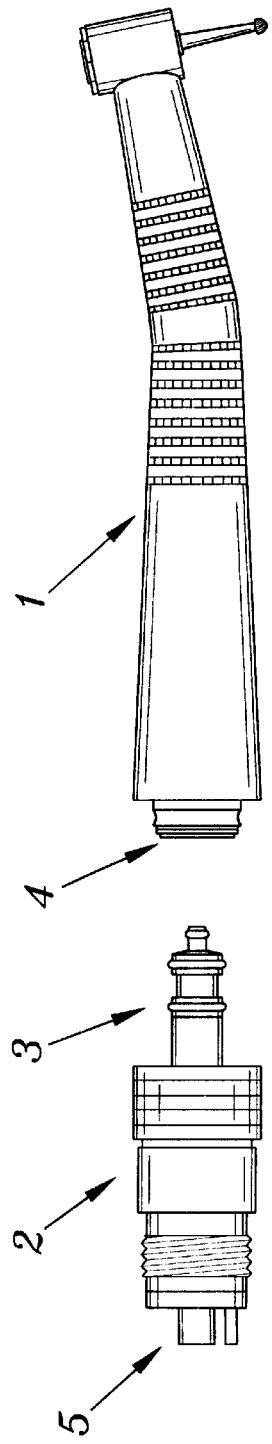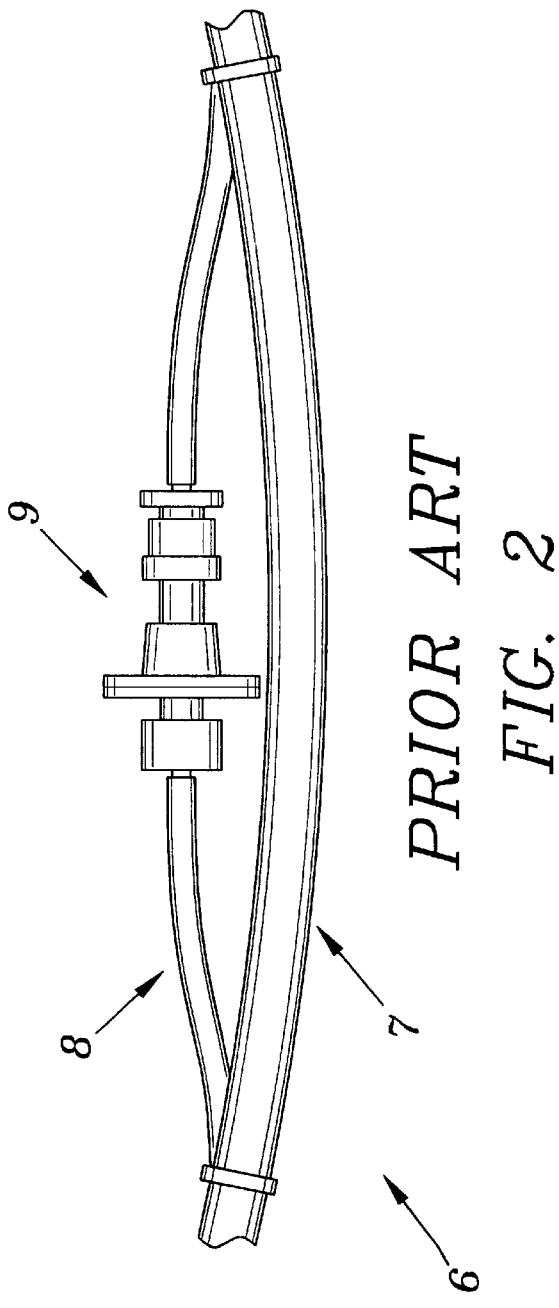
PRIOR ART
FIG. 1
PRIOR ART
FIG. 2

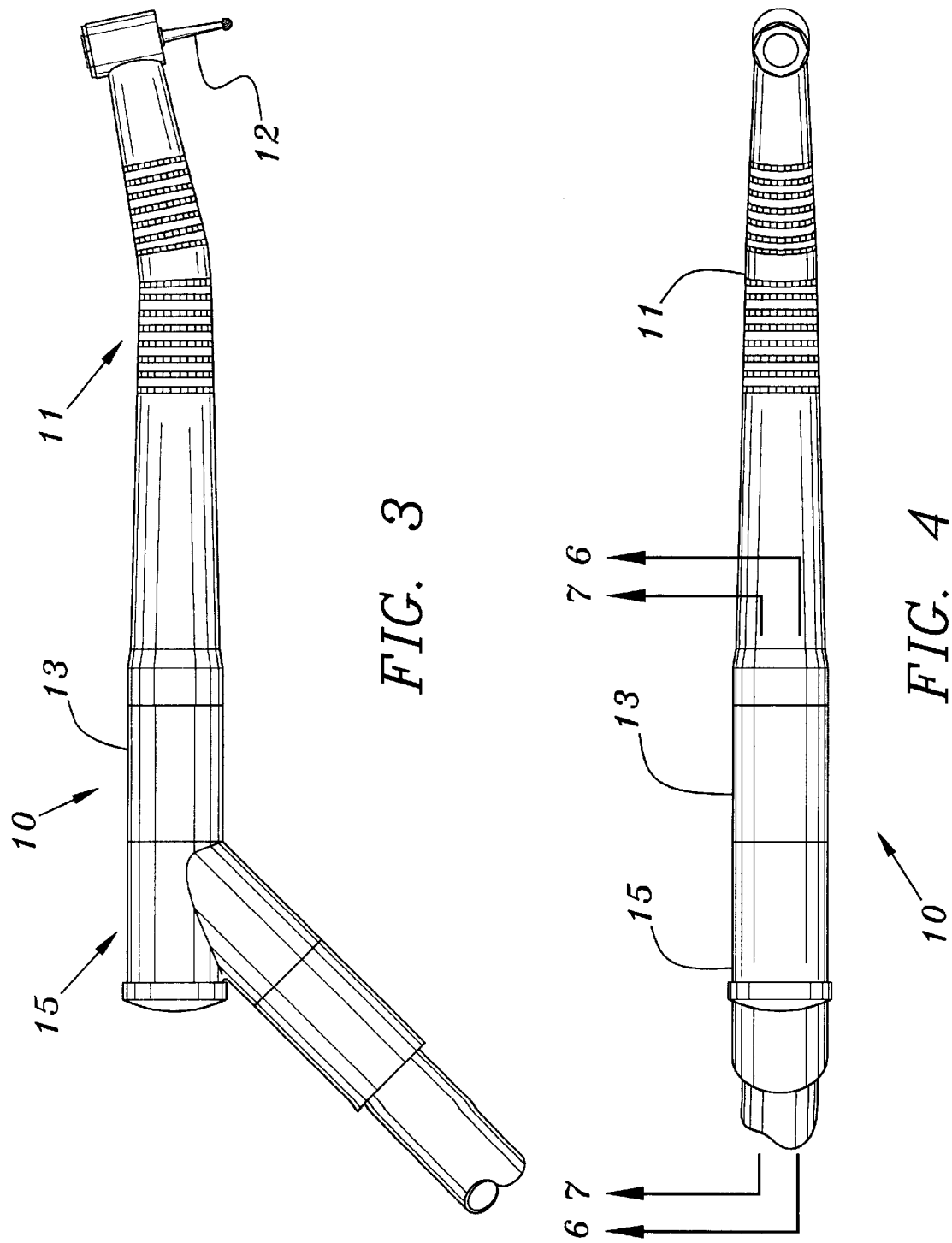

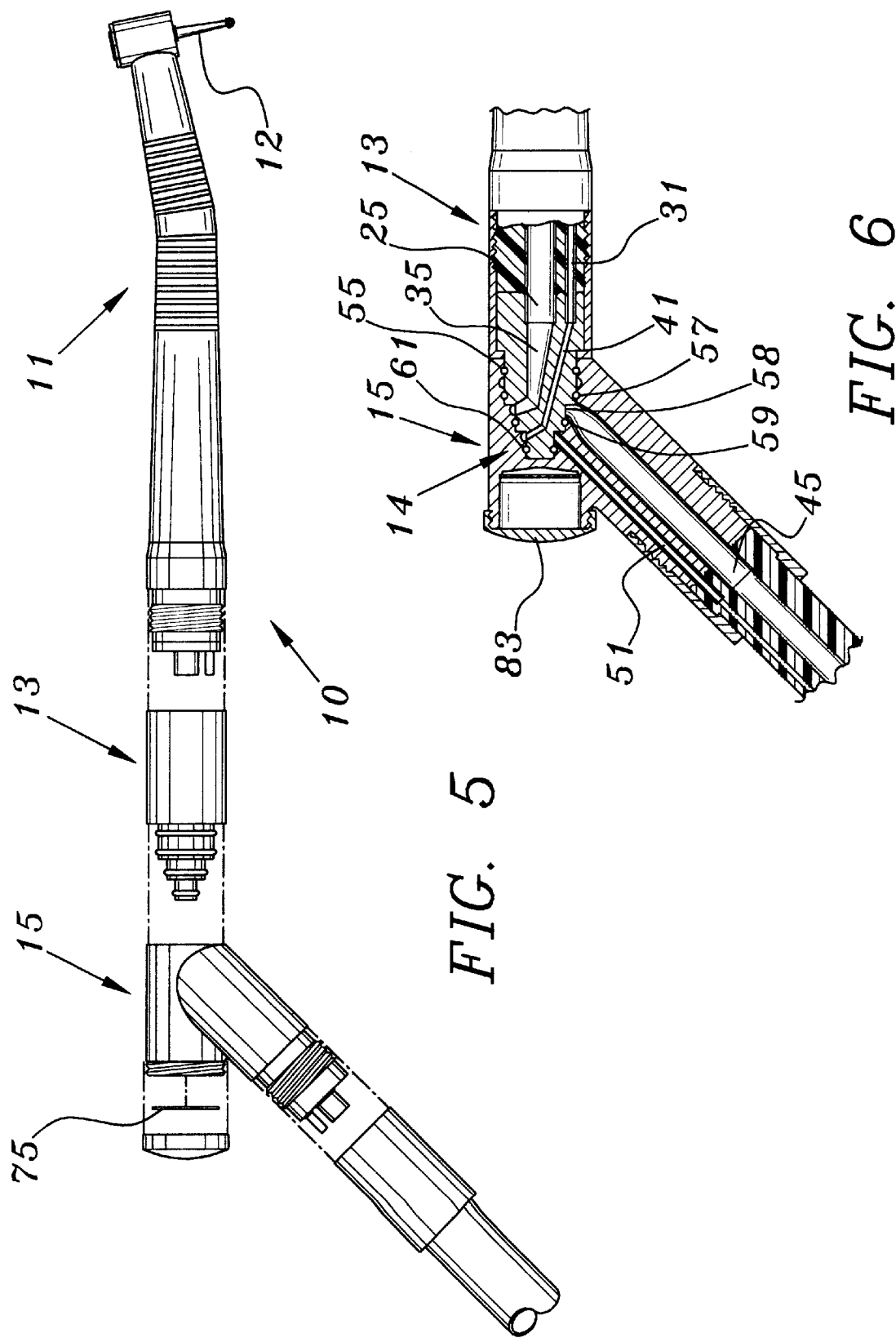

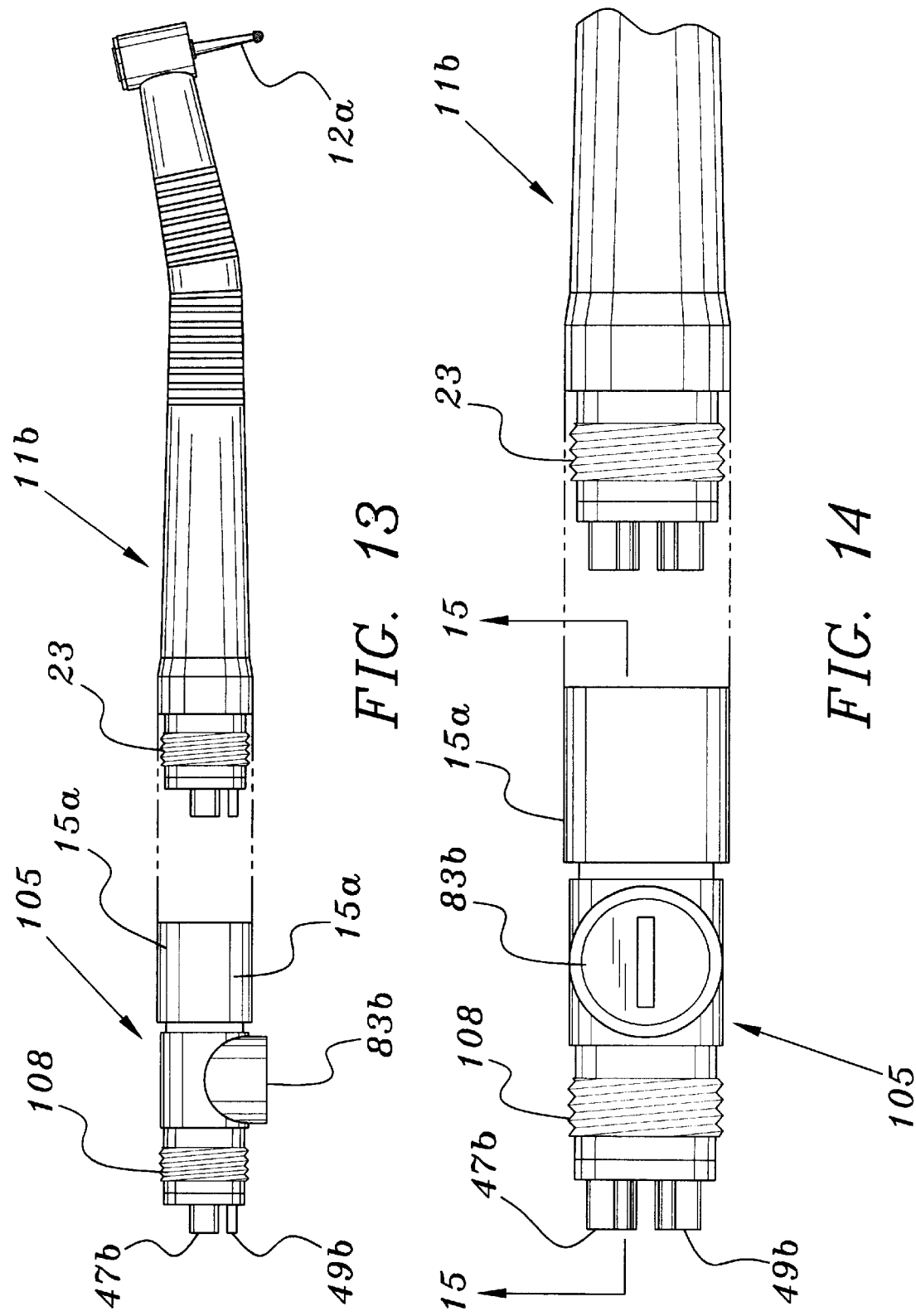

FILTER SYSTEM FOR COUPLING OF A DENTAL HANDPIECE

This application is a continuation-in-part from application Ser. No. 09/209,579, filed Dec. 11, 1998, abandoned.

BACKGROUND OF THE INVENTION

The present invention relates to a filter system for coupling to a dental handpiece. Bio film-derived dental unit waterline contamination is an emerging concern in the dental industry. Accumulated scientific evidence suggests that the potential exposure of dental personnel and patients to high concentrations of microbes may present a risk of infection. Although there is no current epidemiologic evidence of a public health threat, human pathogens including Pseudomonas, Legionella, and nontuberculous Mycobacterium species have been isolated within dental water lines. When a patient is immunologically suppressed, there is a potential risk of contracting serious illness upon being exposed to these human pathogens.

The Center for Disease Control (CDC) has recognized the importance of using sterile irrigation water for surgical procedures. The American Dental Association (ADA) has further recommended that by the year 2000, water for nonsurgical procedures should contain no more than 200 colony forming units (cfu) per millimeter of aerobic, mesophilic, heterotrophic bacteria in the output of a dental air-water syringe or handpiece. While the use of sterile water sources and flushing and purging of waterlines assists in reducing bacterial count in the output of a dental air-water syringe, the use of filters, particularly those having a pore size in the range of 0.22 millimicrons will enhance reduction of bacterial count. See The Journal of American Dental Association, Vol. 128, September 1997, article titled "COMPARISON OF DENTAL WATER QUALITY MANAGEMENT PROCEDURES".

At present, a simple, inexpensive, low maintenance solution to the problem of biofilm accumulation does not exist.

In studies comparing bacteria accumulation on polyethylene tubing as compared to inert glass surfaces, it was found that after 33 days in which flowing drinking water passed therethrough, there was 55 times more bacteria on the polyethylene tubing than on the inert glass surfaces. Small bore plastic tubing has been used in the field of dentistry for many years and such tubing is particularly susceptible to accumulation of biofilm containing human pathogens. Scientific literature suggests that virtually all dental units connected to public water supplies, where the dental units have not been treated or are not using point of use filtration systems, will generally far exceed 200 colony forming units per millimeter of aerobic, mesophilic, heterotrophic bacteria, the limit as recommended by the ADA and CDC guidelines for water quality.

In that it has been recommended that all major manufacturers of dental equipment be in compliance with ADA and CDC guidelines by the year 2000, a need has developed for an actual point of use filter system for dental handpieces that will facilitate such compliance.

Dental manufacturers of new equipment have built-in flushing and purging systems that rely upon bottled, sterile water and bacteriocidal cleaning agents. Such equipment can cost as much as $15,000.00 per room and maintenance employed in using these flushing and purging systems can take as long as 30 minutes per day. While the new equipment solves the compliance problem, it is expensive to purchase and time-consuming to operate. It also poses the risk of accidental spraying of disinfectant agents into the patient's mouth if not properly maintained.

Some manufacturers have developed in-line filters that are installed in the water supply line upstream of the handpiece connector or the connector to the dental handpiece. Manufacturers recommend that these filters be changed daily and, at the current cost of $2.00 per filter-line, the expense builds up over time while the dentist must ensure that daily changing of the filter has been carried out. Additionally, the short length of tubing that is provided to interpose the filter in the water system may become contaminated with biofilm. Such a retro-fit solution is illustrated in FIG. 2 that shows the waterline 8 with the in-line filter system 9 retro-fit therein.

As such, a need has developed for a system that may be employed inexpensively and easily to purify the water entering dental units so that a dentist will be encouraged to purchase and use such a system. It is with these needs in mind that the present invention was developed.

SUMMARY OF THE INVENTION

The present invention relates to a filter system for coupling to a dental handpiece. The present invention includes the following interrelated objects, aspects and features:

(1) In a first aspect, the present invention is contemplated for use within a coupling system supplying air and water to the dental handpiece.

(2) The coupling system includes a series of axially and radially spaced annular couplings on an adapter, each of which supplies one of water, air supply, tool drive air supply or conveys exhaust air. The adapter permits use with standard handpieces.

(3) The filter consists of a small autoclavable glass fiber filter plate mounted under a cap at the proximal end of the coupling at the distal end of a chamber that receives water from the water source.

(4) Water from the water source is conveyed into the chamber, passes through the filter plate, and is conveyed through the coupling to the handpiece where it may be sprayed in the patient's mouth.

(5) A cap is threadably mounted on the coupling to close the chamber and the cap may be removed to either clean or replace the filter.

As such, it is a first object of the present invention to provide a filter system for use in a dental handpiece.

It is a further object of the present invention to provide such a system wherein the coupling includes axially and radially spaced annular couplings.

It is a yet further object of the present invention to provide such a system wherein the water supply flows centrally through the coupling.

It is a still further object of the present invention to provide such a system wherein the filter element is contained within a proximal chamber closed by a cap.

These and other objects, aspects and features of the present invention will be better understood from the following detailed description of the preferred embodiment when read in conjunction with the appended drawing figures.

BRIEF DESCRIPTION OF THE DRAWINGS

FIG. 1 shows an exploded side view of a prior art dental tool coupling.

FIG. 2 shows a side view of a prior art device containing a filter cartridge.

FIG. 3 shows a side view of a dental unit having a coupling in accordance with the teachings of the present invention.

FIG. 4 shows a top view of the dental unit of FIG. 3.

FIG. 5 shows an exploded side view of the dental unit shown in FIGS. 3 and 4.

FIG. 6 shows a cross-sectional view along the line 6—6 of FIG. 4.

FIG. 13 shows an enlarged side view of aa second alternate coupling of the present invention.

FIG. 14 shows an enlarged top view of the second alternate coupling of FIG. 13.

SPECIFIC DESCRIPTION OF THE PREFERRED EMBODIMENT

Figure 7:
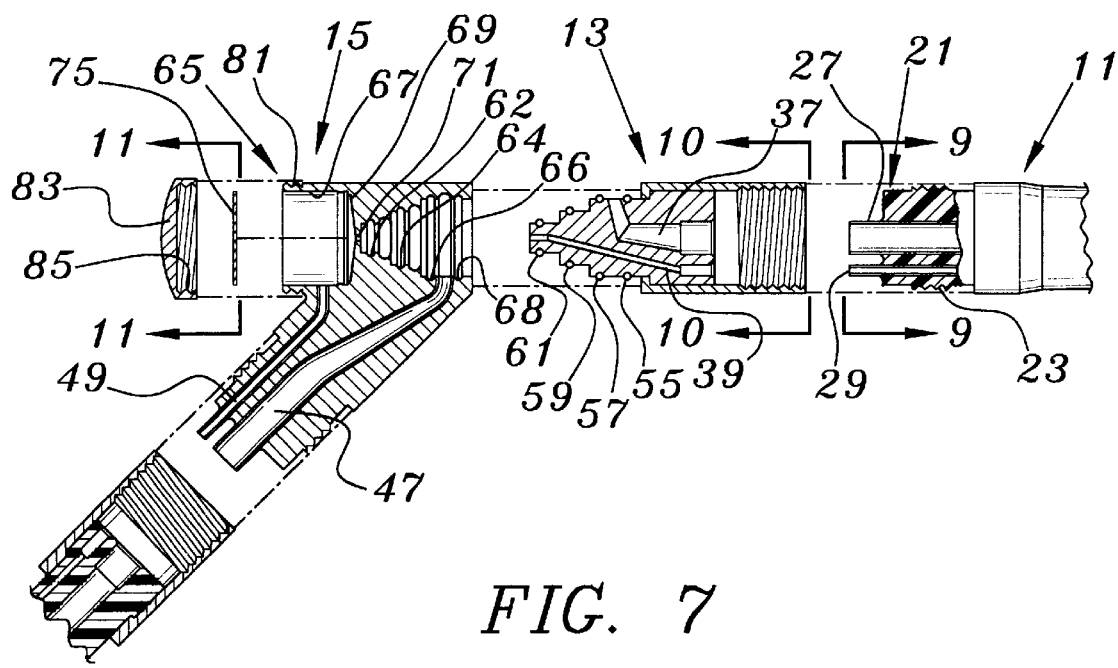
FIG. 7 shows a cross-sectional view along the line 7—7 of FIG. 4.

With reference, first, to FIG. 1, a typical dental handpiece system includes a handpiece 1 having a female coupling 4 that is configured to receive the male coupling 3 of the portion 2 that is connectable to sources of air and water via the coupling 5.

FIG. 2 shows a further prior art system generally designated by the reference numeral 6 and including an air supply line 7 and a water supply line 8 in which an in-line filter system 9 is installed in the water line 8 upstream of the coupling 5 (FIG. 1) where the water supply is connected to the handpiece 1 via the proximal portion 2.

With reference to FIGS. 3–11, the preferred embodiment of the present invention will now be described. With reference to FIGS. 3, 4 and 5, the inventive handpiece system is generally designated by the reference numeral 10 and is seen to include a handpiece 11 (FIG. 5), an adapter 13, and a proximal coupling 15.

With reference to FIGS. 6–10, in particular, specific details of the proximal coupling 15, adapter 13 and handpiece 11 will be better understood.

Figure 9:
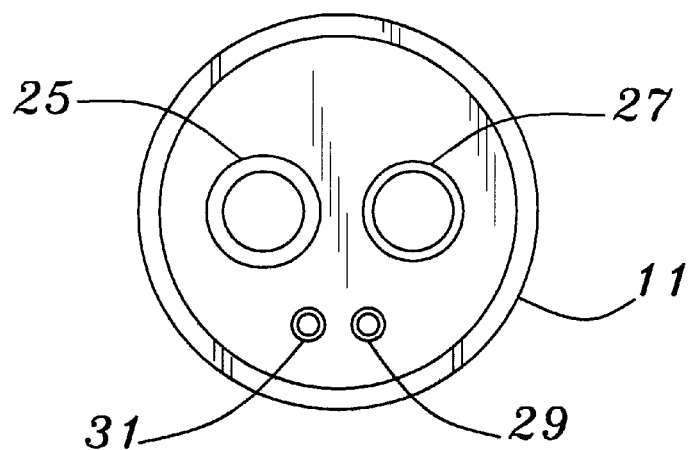
FIG. 9 shows an enlarged cross-sectional view along the line 9—9 of FIG. 7.

With reference, first, to FIGS. 7 and 9, the handpiece 11 is seen to include a proximal end 21 that includes external threads 23 for a purpose to be described in greater detail hereinafter. As seen in FIG. 9, the handpiece 11 includes four conduits 25, 27, 29 and 31 extending therethrough.

As seen in FIG. 7, two of the conduits 27 and 29 are shown. FIG. 6 shows the other two conduits 25 and 31.

In looking at the proximal end of the handpiece 11 and the adapter 13 in FIGS. 6 and 7, it is apparent that the conduit 25 couples with the passageway 35 in the adapter 13, the conduit 27 couples with the passageway 37 in the adapter 13, the conduit 29 couples with the passageway 39 in the adapter 13, and the conduit 31 couples with the passageway 41 in the adapter 13.

With further reference to FIGS. 6 and 7, it is apparent that the passageway 35 in the adapter 13 fluidly couples with the passage 45 in the proximal coupling 15, the passageway 37 in the adapter 13 fluidly couples with the passage 47 in the proximal coupling 15, the passageway 39 in the adapter 13 fluidly couples with the passage 49 in the proximal coupling 15, and the passageway 41 in the adapter 13 fluidly couples with the passage 51 in the proximal coupling 15. The interface between the adapter 13 and the proximal coupling 15 defines a swivel coupling 14 (FIG. 6).

With further reference to FIGS. 6 and 7, it should be understood that the passage 49 is fluidly connected to a source of community water supply, the passage 51 is connected to a source of air that may be conveyed in a dental handpiece and sprayed in the patient's mouth, the passage 45 is connected to a source of drive air that is conveyed through the tool system 10 and causes driving of the end tool 12, best seen in FIGS. 3 and 5. The passage 47 is provided to exhaust air that is used to drive the end tool 12.

Figure 8:
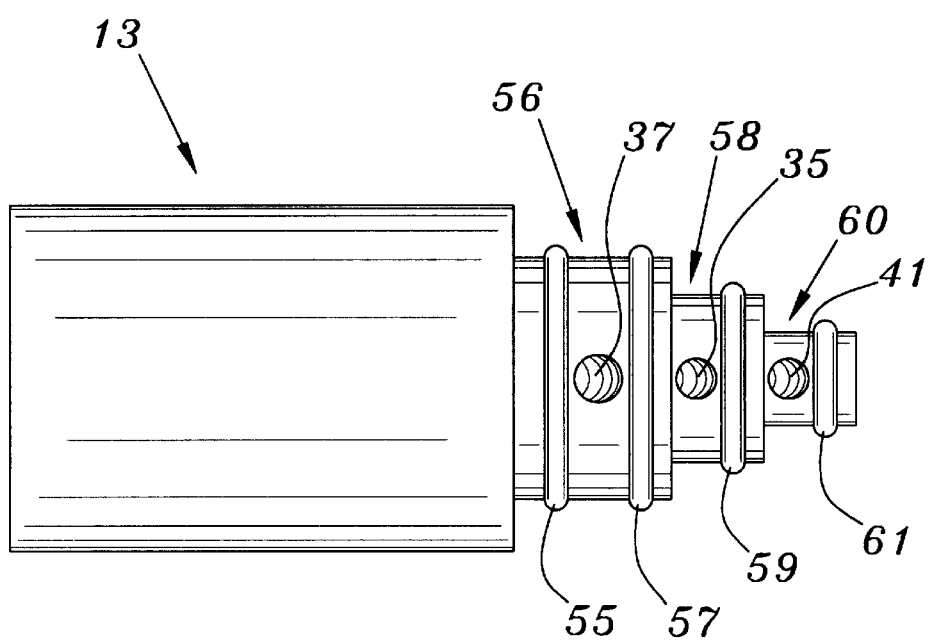
FIG. 8 shows an enlarged side view of a portion of the coupling of the present invention.
Figure 10:
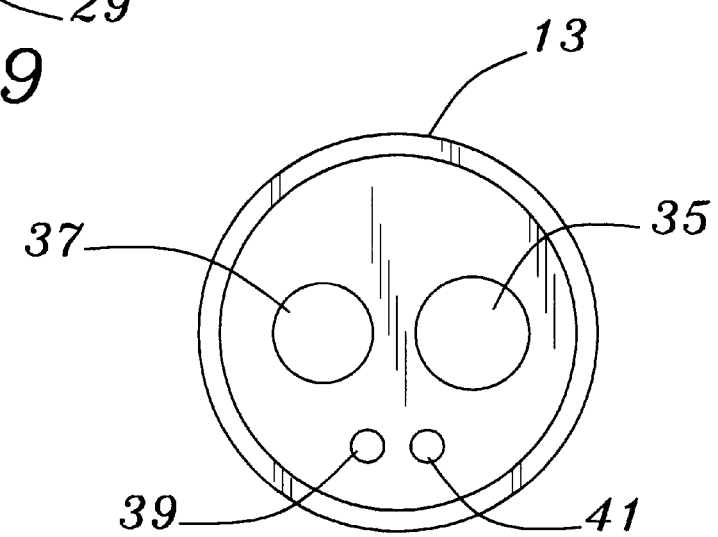
FIG. 10 shows an enlarged cross-sectional view along the line 10—10 of FIG. 7.
Figure 11:
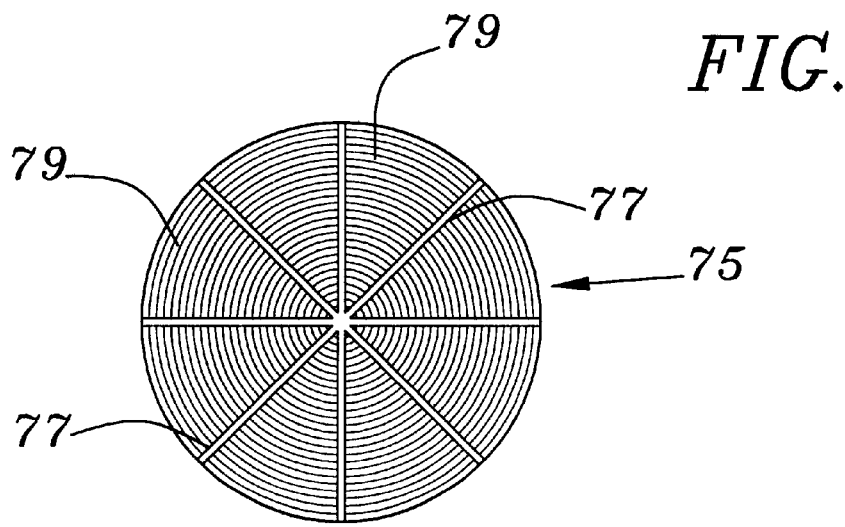
FIG. 11 shows a top view of the filter plate of the present invention.

FIG. 8 shows the adapter 13 enlarged to show details including the ends of the passageways 41, 35 and 37. Also seen in FIGS. 8 and 10 are the O-rings 55, 57, 59 and 61, with the O-rings 55 and 57 surrounding the passageway 37 and defining an annular chamber 56, with the O-rings 57 and 59 surrounding the passageway 35 and creating an annular chamber 58, and with the O-rings 59 and 61 surrounding the passageway 41 and defining an annular chamber 60. As best seen in FIGS. 6 and 7, the O-rings 55, 57, 59 and 61 are respectively received in annular grooves 68, 66, 64 and 62 when the adapter 13 is coupled to the proximal coupling 15. The adapter 13 is designed to couple with standard handpieces, such as the handpiece 11, by use of threads 23 to threadably join the adapter 13 and handpiece 11 and provide a quick disconnect. The user can employ the present invention without the need to discard standard handpieces 11.

As seen in FIGS. 6 and 7 with particular reference to FIG. 6, for example, the passage 45 enters the chamber 58 misaligned from the passageway 35 with the chamber 58 allowing drive air to travel between the passage 45 and the passageway 35 and thence to the conduit 25 through the handpiece 11.

With particular reference to FIGS. 6 and 7, it is seen that the proximal coupling 15 includes a proximal end 65 in which a filter chamber 67 is formed having a distal conical wall 69 with a centrally located port 71 fluidly connected to the passageway 39 when the adapter 13 is coupled to the proximal coupling 15 in the manner shown in FIG. 6 but with the passageways 39 and the port 71 seen in FIG. 7. A filter 75 consists of a flat plate (FIG. 11) having radially extending solid portions 77 between which strainer portions 79 are provided, with the strainer portions providing filtration, for example, with a pore size of no greater than 0.22 millimicrons, a pore size small enough to filter known bacteria.

The filter plate 75 is inserted within the filter chamber 67 in the manner shown in FIGS. 6 and 7. The proximal end 65 of the proximal coupling 15 has external threads 81 that are complementary to the internal threads 85 of a cap 83 that may be threaded thereover to close the chamber 67.

As should be understood, particularly from FIG. 7 and when taken in conjunction with FIG. 6, water may flow through the passage 49 from a source of community water supply (not shown) and may enter the chamber 67 whereupon it passes through the filter plate 75 and thence through the passageway 39 and the conduit 29 to the handpiece 11 where such water may be sprayed into the patient's mouth under the control of a valve (not shown). When it is desired to replace the filter plate 75, it is easy to unscrew the cap 83 and remove the filter plate 75, whereupon the filter plate 75 may be restored within the chamber 67 and the cap 83 replaced to the position shown in FIG. 6 ready for use.

The filter plate may be made of a strong material such as glass fiber to provide the desired pore size. The filter plate 75 is designed to be autoclavable and, as should be understood from the above description, to be easily accessible.

The other flow paths described herein for blowing air, drive air and exhaust air are provided in the inventive system so that it is versatile and usable with any similar dental handpiece.

The inventive filter plate 75 is made of a material allowing it to be subjected to multiple autoclave cycles while retained within the chamber 67 of the proximal coupling 15 so that additional routines to the sterilization process are avoided. Thus, the entire assembly of adapter 13 and proximal coupling 15 may be autoclaved without disassembly. Periodically, the filter plate 75 is discarded and replaced with a new filter plate 75 when water flow is hindered by clogging of the filter pores.

Due to the creation of the chambers 56, 58 and 60 by the O-rings 55, 57, 59 and 61, the adapter 13 may swivel with respect to the proximal coupling 15 with connection being maintained between the various conduits and passageways at all times.

Figure 12:
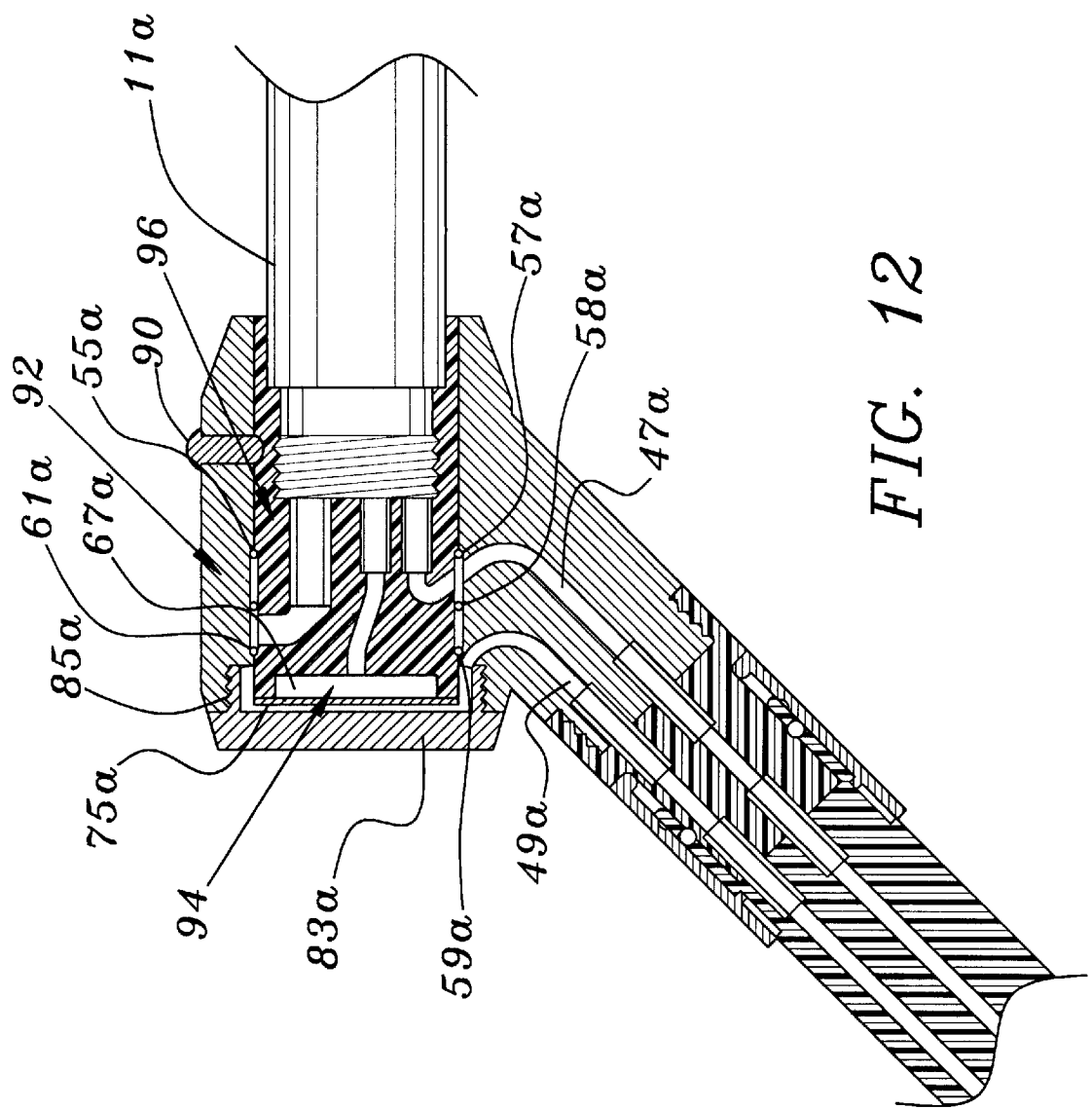
FIG. 12 shows a side sectional view of an alternate embodiment of the invention.

A variation of the handpiece filter assembly herein previously discussed is set forth in FIG. 12 whereby only the filter assembly 94 and swivel coupling 92 are included, leaving out the quick disconnect feature that was previously described in this application. This variation shortens the previous filter assembly and changes the internal swivel design as it pertains to the internal swivel mechanism. The remaining aspects of the invention function as in the original design features with a water passageway 49a and exhaust air passageway 47a.

This modification reduces the size of the filter connector and therefor has the advantage of shortening the length of the filter assembly connector. This modification further allows dentists a choice in design without changing the function of the connector, which is to filter the water at the point of use. The shortened design also allows for a similar length and feel as the existing handpiece connectors already used in dentistry. Balance and weight distribution are important to many dentists. This modification as just described would be autoclavable as a unit when connected to the dental handpiece. It would only lack the quick disconnect feature, which is only a slight time savings over unscrewing the handpiece from the handpiece connector attached to the air/water lines.

Both designs offer precise point of use filtration of water and both are a simple means of reaching CDC and ADA compliance limits on waterborne pathogens ((200 cfu's)'s). These designs offer precise point of use water filtration in a simple handpiece connector that is entirely autoclavable. No further maintenance is needed. No closed bottled water systems and no harsh chemical purging of the water lines are necessary. There are no expensive dental equipment purchases and no daily or weekly filter changes. The filter in this invention is changed only when water flow is diminished due to the clogging of the filter pores.

As to the internal design changes on the variation of FIG. 12, it should be noted that the only difference is in deletion of the quick disconnect feature. Therefore, it is unnecessary that the internal o-ring assembly as part of the connector be reversed to compress the design into a smaller space. With this design variation, the o-ring assembly 96 can only be removed by unscrewing the filter cap 83a. The internal design feature allows for the dental handpiece 11a to be threaded 85a into the filter-swivel connector 92 by compressing the locking pin 90 which holds the internal swivel secure. Once the handpiece 11a is threaded in place, it becomes one piece with the filter-swivel connector and can then be removed along with that filter-swivel connector from the dental unit water-line and autoclaved after each use.

This alternative design variation includes an o-ring connector 96 containing o-rings 55a, 57a, 58a, 59a and 61a designed to allow the handpiece to swivel within the connector and yet still keep the air and water lines active to allow the handpiece to function appropriately while used in the mouth for patient care.

The design of FIG. 12 is a two-part design that allows for the swivel/o-ring unit to be attached to the posterior threaded end of the dental handpiece, allowing this section to be removed from the angled filter-connector unit. The benefit is that another handpiece could be coupled easily to the same angled filter-connector.

This benefit would be useful when changing to the Eraser—Air-polishing system by Parkell, the Star Sonic scaler and other similar air driven abrasive or cleaning devices used in dentistry where a quick disconnect feature would be useful. This feature would be helpful when multiple procedures are completed on the same patient. The single filter connector could be used with different dental devices while using only one sterile filter handpiece connector unit attached to a dental air/water line.

FIGS. 13–16 show an alternate configuration for a proximal coupler 15a. The handpiece tool 11b engages the coupler 15a via threads 23 as used on all the handpiece tools 11, 11a and 11b. Threads 108 at a proximal end of coupler 15a provides engagement of the exhaust air passageway 47b and the water passageway 49b to their respective exhaust air outlet and water line.

Figure 15:
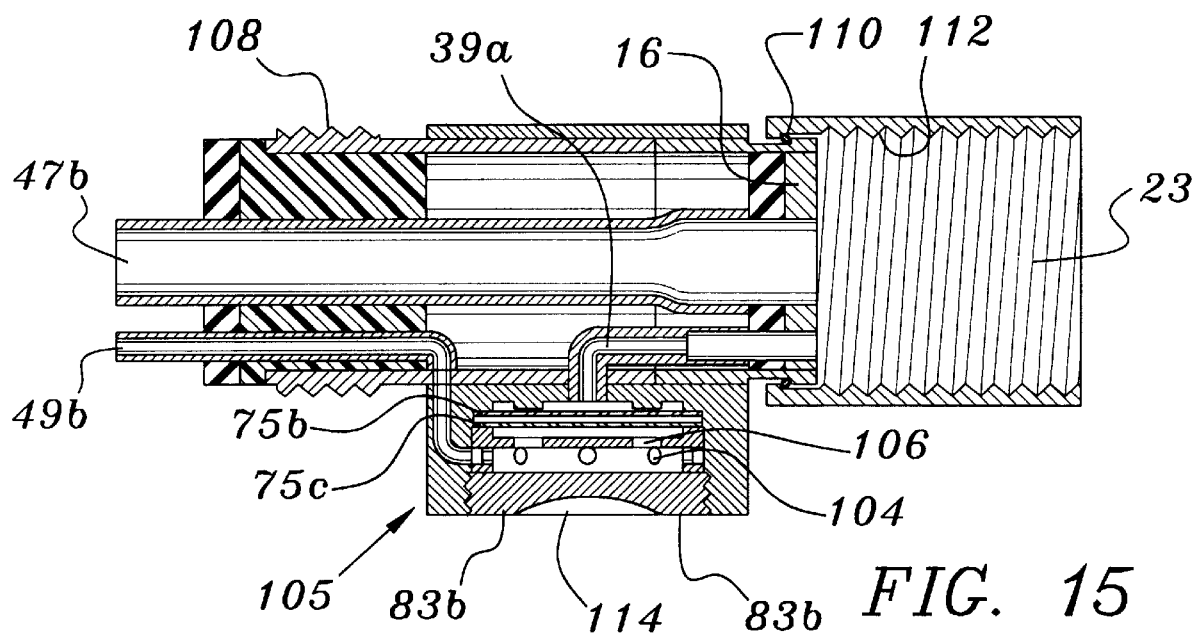
FIG. 15 shows a cross-sectional view along line 15—15 in FIG. 14.
Figure 16:
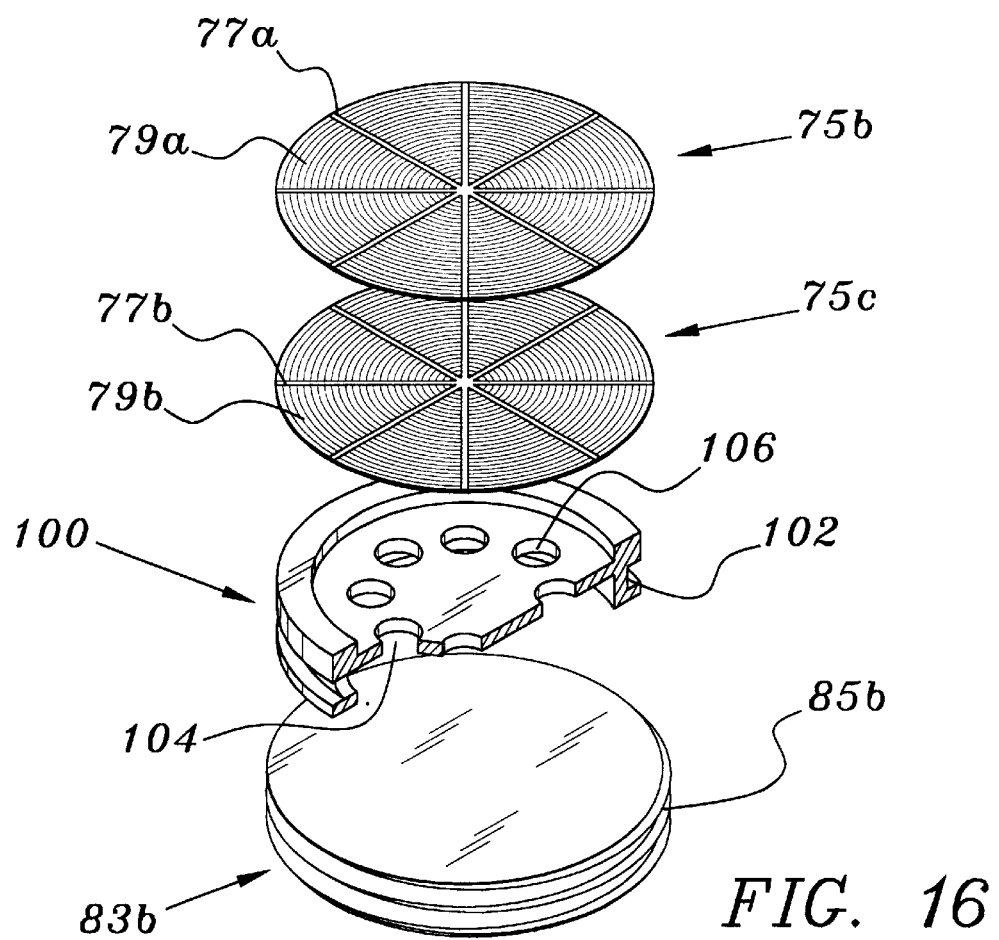
FIG. 16 shows an exploded view of the filter apparatus used in alternate coupling for the dental tool.

The coupler 15a has a filter connector 105 that has an external cap 83b with an indent 114. As seen in FIGS. 15–16 the cap 83b is threaded to the filter connector 105 via threads 85b. A water guide disc 100 is juxtaposed to an inside surface of the disc filter cap 83b. An annular water channel 102 traverses the exterior of disc 100 so that water can travel around the disc 100 into holes 104, through holes 106 and into the filters 75c and 75b respectively. Each filter has a solid portion 77a or 77b and a strainer portion 79a and 79b. The filters 75b general filters out particles larger than 5 microns and 75a filters out particles larger than 0.2 millimicrons.

FIG. 15 shows the filter connector portion 105 in detail. Passageway 39a receives water via the filters 75c and 75b from passage 49a. Threads 108 enable coupling to the air-water lines. At the other end the threads 23 of the handpiece 11b engage threads 112 of the proximal coupler 15a. A rubber seal 16 and wire ring 100 prevent leakage around the connection between handpiece 11b and the coupler 15a.

This alternate coupler 15a with multiple filters provides another means of adhering to ADA and CDC standards.

Through use of the present invention, the ADA and CDC guidelines recommending compliance with the 200 cfu limit easily may be met.

As such, an invention has been disclosed in terms of a preferred embodiment thereof which fulfills each and every one of the objects of the invention as set forth hereinabove, and provides a new and useful filter system for coupling of dental handpiece of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

What is claimed is:

1. In a system for employing a dental handpiece the dental handpiece having a proximal end and a distal end, said proximal end carrying proximal terminations of at least two conduits, the improvement comprising an adapter—coupling—filter system, comprising;
    a) an adapter having a distal end releasably attachable on said proximal end of said handpiece, a plurality of passageways therethrough, each of said conduits being coupled to one of said passageways when said adapter is attached to said handpiece, said passageways opening at a proximal end of said adapter;
    b) a proximal coupling releasably coupled to said adapter, said proximal coupling including a plurality of passages therethrough, each passage being coupled to one of said passageways when said coupling is coupled to said adapter;
    c) a flow path defined by one passage, one passageway and one conduit, said flow path being adapted to be connected to a source of water, said proximal coupling having a filter chamber including an opening to the exterior, the filter chamber within the proximal coupling fluidly connected to said one passage, and at least one filter within said filter chamber, the at least one filter being accessible for removal after a cap enclosing the opening to the exterior has been removed, wherein water flows through the at least one filter within the filter chamber from said source toward said one passageway.

2. The system of claim 1, wherein said adapter swivels with respect to said proximal coupling.

3. The system of claim 2, wherein when said adapter swivels with respect to said proximal coupling the proximal coupling includes:
    a) distal terminations of said passages coupled to proximal terminations of said passageways at an interface;
    b) said interface having a circular cross-section permitting mutual pivoting between said proximal coupling and said adapter;
    c) said interface including an annular chamber enclosing each connection location between a respective passage and respective passageway.

4. The system of claim 3, wherein each annular chamber is defined by two O-rings attached to one of said adapter or said proximal coupling and seated in respective grooves located in the other of said adapter or said proximal coupling.

5. The system of claim 4, wherein said O-rings are attached to said adapter.

6. The system of claim 1, wherein said one passageway has a proximal termination centrally located on said proximal end of said adapter.

7. The system of claim 3, wherein said one passageway has a proximal termination centrally located on said proximal end of said adapter.

8. The system of claim 1, wherein said filter chamber has a distal wall with a port therethrough fluidly connected to said one passageway.

9. The system of claim 8, wherein said filter chamber has a proximal opening closed by a removable cap.

10. The system of claim 9, wherein said proximal opening has exterior threads and said cap has internal complementary threads.

11. The system of claim 1, wherein said filter comprises a flat plate.

12. The system of claim 11, wherein said plate includes a plurality of openings therethrough having a pore size no greater than 0.22 millimicrons.

13. The system according to claim 1 wherein the proximal coupling contains two filters in the filter chamber.

14. In a dental handpiece having a proximal end and a distal end, said proximal end carrying proximal terminations of at least two conduits, the improvement comprising an adapter—coupling—filter system, comprising;
    a) an adapter having a distal end attachable on said proximal end of said handpiece, a plurality of passageways therethrough, each of said conduits being coupled to one of said passageways when said adapter is attached to said handpiece, said passageways opening at a proximal end of said adapter;
    b) a proximal coupling coupled to said adapter with a coupling, said proximal coupling including a plurality of passages therethrough, each passage being coupled to one of said passageways when said coupling is coupled to said adapter;
    c) a flow path defined by one passage, one passageway having a proximal termination centrally located on said proximal end of said adapter and one conduit, said flow path being connected to a source of water, said proximal coupling having a filter chamber within the proximal coupling fluidly connected to said one passage, and at least one filter within said filter chamber through which water flows from said source toward said one passageway, said filter chamber having a proximal opening closed by a removable cap, the at least one filter being removable through the proximal opening after the cap is removed;
    d) said adapter swiveling with respect to said proximal coupling, said proximal coupling including:
        i) distal terminations of said passages coupled to proximal terminations of said passageways at an interface;
        ii) said interface having a circular cross-section permitting mutual pivoting between said proximal coupling and said adapter;
        iii) said interface including an annular chamber enclosing each connection location between a respective passage and respective passageway.

15. The dental handpiece of claim 14, wherein each annular chamber is defined by two O-rings attached to one of said adapter or said proximal coupling and seated in respective grooves located in the other of said adapter or said proximal coupling.

16. The dental handpiece of claim 14, wherein said O-rings are attached to said adapter.

17. The dental handpiece of claim 14, wherein said filter chamber has a distal wall with a port therethrough fluidly connected to said one passageway.

18. The dental handpiece of claim 14, wherein said filter comprises a flat plate.

19. The dental handpiece of claim 18, wherein said plate includes a plurality of openings therethrough having a pore size no greater than 0.22 Millimicrons.

20. The dental handpiece of claim 14, wherein the filter chamber contains two filters.

21. A dental handpiece having a proximal end and a distal end, said proximal end carrying proximal terminations of at least two conduits, the proximal end of the dental handpiece connected directly to a distal end of a coupler having a self-contained water filtering assembly, a proximal end of the coupler providing engagement with an exhaust air passageway and water passageway, said coupler halving an opening between said proximal and distal ends wherein the water filtering assembly is accessible for changing of filters after a cap covering said opening is removed.

22. The dental handpiece according to claim 21 wherein the water filtering-assembly is one or more filters located in a filter chamber within a proximal portion of the coupler, the coupler distal end swiveling with respect to the proximal end of the handpiece.

23. The dental handpiece according to claim 21 wherein threads at a proximal end of the coupler provide engagement with the exhaust air passageway and the water passageway, the water filter assembly having at least two filters and a water guide disc juxtaposed to an inside surface of a disc filter cap located within a proximal portion of the coupler, the disc filter cap being removable to change the filters within the coupler and the distal end of the coupler threadably engaged to the proximal end of the handpiece.

* * * * *